United States Patent
Rittner et al.

(10) Patent No.: US 9,884,210 B2
(45) Date of Patent: Feb. 6, 2018

(54) AIRCRAFT PASSENGER OXYGEN MASK WITH CLOSED CIRCUIT CONCEPT

(71) Applicant: INTERTECHNIQUE, Plaisir (FR)

(72) Inventors: Wolfgang Rittner, Ahrensbok (DE); Rüdiger Meckes, Berkenthin (DE); Günter Boomgaarden, Scharbeutz (DE); Marco Hollm, Rosdorf (DE)

(73) Assignee: Zodiac Aerotechnics, Plaisir (FR)

( * ) Notice: Subject to any disclaimer, the term of this patent is extended or adjusted under 35 U.S.C. 154(b) by 523 days.

(21) Appl. No.: 13/929,830

(22) Filed: Jun. 28, 2013

(65) Prior Publication Data

US 2014/0000594 A1    Jan. 2, 2014

Related U.S. Application Data (60) Provisional application No. 61/665,486, filed on Jun. 28, 2012.

(51) Int. Cl.
*A62B 7/08*    (2006.01)
*A62B 18/02*    (2006.01)
(Continued)

(52) U.S. Cl.
CPC ............... *A62B 7/08* (2013.01); *A61M 16/20* (2013.01); *A62B 7/00* (2013.01); *A62B 7/02* (2013.01); *A62B 7/14* (2013.01); *A62B 9/02* (2013.01); *A62B 18/02* (2013.01); *A62B 21/00* (2013.01); *B64D 10/00* (2013.01);
(Continued)

(58) Field of Classification Search
CPC .... A62B 7/00; A62B 7/02; A62B 7/08; A62B 7/12; A62B 7/14; A62B 9/04; A62B 18/00; A62B 18/003; A62B 18/02; A62B 19/00; A62B 21/00; A62B 25/005; A62D 9/00; A61M 16/0045; A61M 16/0093; A61M 16/06; A61M 16/22; A61M 2202/0078;
(Continued)

(56) References Cited

U.S. PATENT DOCUMENTS 3,208,449 A * 9/1965 Bartlett, Jr. ............ A61M 16/00
128/202.27
3,229,681 A * 1/1966 Gluckstein ......... A41D 13/0051
126/204

(Continued)

FOREIGN PATENT DOCUMENTS

CN    1990067    7/2007

OTHER PUBLICATIONS

U.S. Appl. No. 13/929,820, Office Action dated Aug. 28, 2015.
(Continued)

*Primary Examiner* — (Jackie) Tan-Uyen T Ho
*Assistant Examiner* — Joseph D Boecker
(74) *Attorney, Agent, or Firm* — Hodgson Russ LLP (57) ABSTRACT

The invention relates to an aircraft passenger emergency oxygen supply device comprising an oxygen mask having a mask body with a first opening for covering mouth and/or nose of the passenger, a second opening connecting said first opening with a source of oxygen, a passenger service unit, a connecting line fixed to the oxygen mask body at one end and having a coupling at the other end for coupling said line to the passenger service unit wherein a chemical reaction component is comprised in the oxygen mask.

8 Claims, 4 Drawing Sheets

(51) Int. Cl.
*A62B 7/02* (2006.01)
*A62B 7/14* (2006.01)
*A62B 9/02* (2006.01)
*A61M 16/20* (2006.01)
*A62B 7/00* (2006.01)
*B64D 11/00* (2006.01)
*A62B 21/00* (2006.01)
*B64D 10/00* (2006.01)
*C01B 13/02* (2006.01)
*G08B 5/22* (2006.01)
*G08B 5/00* (2006.01)
*G08B 5/36* (2006.01)

(52) U.S. Cl.
CPC ...... B64D 11/0015 (2013.01); C01B 13/0296 (2013.01); *B64D 11/00155* (2014.12); *B64D 2231/00* (2013.01); *B64D 2231/02* (2013.01); *G08B 5/00* (2013.01); *G08B 5/224* (2013.01); *G08B 5/36* (2013.01)

(58) Field of Classification Search
CPC .......... A61M 2202/0208; B64D 10/00; B64D 2231/00; B64D 2231/025
USPC .................. 128/200.28, 201.25, 202.26, 128/205.27–205.29, 206.12, 206.17
See application file for complete search history.

(56) References Cited

U.S. PATENT DOCUMENTS

| | | | | |
|---|---|---|---|---|
| 4,016,878 A | * | 4/1977 | Castel | A61M 16/1075 126/204 |
| 4,793,342 A | | 12/1988 | Haber | |
| 5,007,421 A | * | 4/1991 | Stewart | A62B 17/006 128/204.18 |
| 5,115,804 A | * | 5/1992 | Brookman | A62B 18/025 128/201.22 |
| 5,265,597 A | * | 11/1993 | Wallis | A62B 18/025 128/205.17 |
| 5,394,867 A | | 3/1995 | Swann | |
| 5,690,099 A | * | 11/1997 | Abramov | A62B 19/02 128/202.26 |
| 5,850,833 A | | 12/1998 | Kotliar | |
| 6,340,024 B1 | | 1/2002 | Brookman et al. | |
| 6,478,850 B1 | | 11/2002 | Warren | |
| 7,066,985 B2 | | 6/2006 | Deane et al. | |
| 7,329,304 B2 | | 2/2008 | Bliss et al. | |
| 8,016,925 B2 | | 9/2011 | McCombs et al. | |
| 8,794,237 B2 | | 8/2014 | Wilkinson et al. | |
| 2004/0134493 A1 | | 7/2004 | McCombs et al. | |
| 2004/0245390 A1 | | 12/2004 | Meckes et al. | |
| 2005/0051029 A1 | | 3/2005 | Lloyd | |
| 2006/0118115 A1 | * | 6/2006 | Cannon | A62B 7/14 128/204.26 |
| 2008/0202511 A1 | | 8/2008 | Meckes et al. | |
| 2008/0245370 A1 | * | 10/2008 | Kobziar | A62B 7/14 128/206.21 |
| 2010/0101578 A1 | * | 4/2010 | Cha | A61B 5/087 128/205.24 |
| 2014/0007869 A1 | | 1/2014 | Rittner et al. | |

OTHER PUBLICATIONS

Ceca, "Medical oxygen concentrator (MEDOX)", retrieved from https ://web. archive. o rg/web/20130303085909/http :/ /www .cecach em icals. co m/e n/expe rtise/ molecular -s i eves/medical-oxygenconcentrators/index. html with date Mar. 3, 2013.

Final Office Action for U.S. Appl. No. 13/929,820, dated Feb. 25, 2016, 14 pages.

First Office Action for Chinese Patent Application No. CN201310269699.7, dated Jan. 28,2016, 10 pages (6 pages English translation, 4 pages original).

* cited by examiner

AIRCRAFT PASSENGER OXYGEN MASK WITH CLOSED CIRCUIT CONCEPT

CROSS-REFERENCE TO RELATED APPLICATION

This application claims the benefit of and priority to U.S. Provisional Application No. 61/665,486 filed on Jun. 28, 2012, the contents of which are incorporated herein by reference.

FIELD OF THE INVENTION

The invention relates to an aircraft passenger emergency oxygen supply device comprising an oxygen mask having a mask body with a first opening for covering mouth and/or nose of the passenger, a second opening connecting said first opening with a source of oxygen, a passenger service unit, a connecting line fixed to the oxygen mask body at one end and having a coupling at the other end for coupling said line to the passenger service unit. The further aspect of the invention is a method for rescuing a passenger of an aircraft in an emergency situation.

BACKGROUND OF THE INVENTION

Emergency situations on board of an aircraft may be characterized by a decompression of the cabin, smoke or fire, wind turbulences and mechanical impacts. Usually, a pilot will seek to conduct a quick emergency descent of the aircraft in such an emergency situation and to reach the closest airport or emergency landing lane. After landing the aircraft, a quick exit of all passengers out of the aircraft is required. Such quick exit may be hindered by smoke and/or insufficient oxygen in the aircraft passenger cabin.

It is known to supply oxygen to passengers in an emergency situation like a decompression situation, smoke or fire in the cabin. For this purpose, oxygen masks drop out of a passenger service unit and oxygen is supplied to the passenger via said oxygen mask. The oxygen mask is connected to the passenger service unit via a connecting line. In the passenger service unit an oxygen source is comprised which stores oxygen and provides said oxygen to the passenger after activation of the oxygen supply. Usually, the passenger can activate the oxygen supply pulling a connecting line wherein said connecting line may be a flexible tube which at the same time serves to direct the oxygen from the passenger service unit to the oxygen mask or maybe a wire or rope or the like distinct from the connecting line. It is known to store oxygen in the passenger service unit in a chemically bound form and to produce said oxygen in a chemical reaction after activation. This type of oxygen source is called chemical oxygen generator (COG). It is further known to store oxygen in a pressurized tank wherein activation of said oxygen source comprises opening a valve or a sealing component to open said pressure tank and allow flow of oxygen out of said tank to the oxygen mask.

Such emergency oxygen devices have shown to be insufficient in certain emergency situations, in particular in case of smoke of fire in the cabin or during the quick exit of the passengers out of the cabin. It is an object of the invention to provide an emergency oxygen supply device for passengers of an aircraft which improves the safety of the passenger in such emergency situations and facilitates the handling of the emergency oxygen supply device by the passenger.

SUMMARY OF THE INVENTION

This object is solved by an aircraft passenger emergency oxygen supply device as described in the introductory portion wherein the oxygen mask comprises a chemical reaction component connected to the mask body for receiving exhaled air out of said mask body, converting said exhaled air into supply air by a chemical reaction between said exhaled air and a chemical reaction material comprised in said chemical reaction component to produce oxygen-enriched air and for supplying said oxygen-enriched air as the supply air to the mask body.

According to the invention a chemical reaction component is comprised in the oxygen mask. The oxygen mask is thus characterized by a chemical reaction component which is part of the oxygen mask or integral with the oxygen mask or directly attached to the oxygen mask. This means that the chemical reaction component is mechanically fixed to the mask in such a way that the passenger carries the chemical reaction component together with the oxygen mask. In contrast to prior art oxygen emergency systems for aircraft passenger a chemical reaction component is provided which allows to convert exhaled air of the passenger into oxygen enriched and optionally carbon dioxide depleted air which can be inhaled by the passenger again. By this, the passenger receives an independent oxygen mask and can carry this oxygen mask and receive oxygen out of the mask body even if the passenger leaves his seat like this may happen e.g. in a panic situation or may be required in a quick exit procedure.

One advantage of the emergency oxygen supply device according to the invention is to allow the passenger to leave his seat and still be supplied with oxygen which protects the passenger from smoke or hypoxia in an emergency situation. In particular if a quick exit procedure is conducted on board of the aircraft this significantly increases the safety of the passenger since the passenger may even wait for several minutes in a row inside the aircraft cabin before exiting the cabin through an emergency exit and is not endangered by smoke or reduced oxygen content in the air inside the cabin.

According to a first aspect of the invention said connecting line is an oxygen supply line for connecting said mask body with a source of oxygen in said passenger service unit, wherein said source of oxygen is a chemical oxygen generator or a pressurized oxygen tank.

According to the invention, the chemical reaction component is adapted to produce oxygen enriched air out of the exhaled air of the passenger. Thus, the chemical reaction component comprises a chemical reaction material which is capable to produce oxygen out of the exhaled air comprising carbon dioxide. However, usually such chemical reaction materials which are adapted to convert oxygen depleted air into oxygen enriched air require some start-up time to provide said oxygen enriched air. During this start-up time the passenger may be supplied from a source of oxygen which is capable of immediate release of oxygen in an emergency situation. Such source of oxygen may be a chemical oxygen generator comprising a chemical reaction material which is producing oxygen independently from exhaled air in a chemical reaction or may be a pressurized oxygen tank comprising oxygen in pressurized form. According to this preferred embodiment the connecting line is a flexible tube or hose and the source of oxygen is arranged in said passenger service unit. In such case, the connecting line is required for providing initial start-up oxygen out of said source of oxygen to the oxygen mask to immediately supply the passenger with oxygen in an emergency situation. After a short start-up time during which the passenger is supplied via said connecting line out of the source of oxygen in the passenger service unit the chemical reaction material comprised in the oxygen mask will have started up the chemical reaction to convert exhaled oxygen depleted air into oxygen enriched air and to thus supply the passenger with oxygen enriched air independent from the source of oxygen.

According to an alternative preferred embodiment hereto said connecting line is a wire or rope for connecting said mask body with a fixing point in said passenger service unit, wherein said oxygen mask further comprises a source of oxygen, wherein said source of oxygen is a chemical oxygen generator or a pressurized oxygen tank. According to this embodiment, again a source of oxygen is comprised in the oxygen supply device to provide oxygen in the initial start-up time period wherein the chemical reaction material comprised in the chemical reaction component does not sufficiently enrich the exhaled air with oxygen for supplying oxygen enriched air to the passenger. In this embodiment the source of oxygen is comprised in the oxygen mask, i.e. is a part of the oxygen mask, integral with the oxygen mask or directly fixed to the oxygen mask. In such a case the connecting line is not required to direct or deliver oxygen out of the passenger service unit to the oxygen mask but may be a simple wire or rope or the like which serves to hold the oxygen mask after it has fallen out of the passenger service unit or which may serve to activate the oxygen supply by imparting a pulling force onto said connecting line to activate a switch element coupled with said connecting line.

According to a further preferred embodiment said connecting line comprises a coupling element, said coupling element being adapted to maintain the connection provided by said connecting line and said coupling between the oxygen mask and the passenger service unit if a predetermined pulling force along said connecting line is not exceeded and to release said connection provided by said connecting line and said coupling between the oxygen mask and the passenger service unit if a predetermined lower pulling force along said connecting line is exceeded.

According to this embodiment the passenger may disconnect the oxygen mask from the passenger service unit by detaching the connecting line a coupling element. This coupling element is adapted to maintain the connection between the passenger service unit and the oxygen mask up to predetermined pulling force which is applied along said connecting line by the passenger. If said pulling force is exceeded the coupling element releases the oxygen mask to thus allow the passenger to leave his seat with the oxygen mask and to be supplied with oxygen furtheron. The coupling element may be positioned at the oxygen mask or at the passenger service unit or in between along the connecting line. It may comprises to connecting elements coupled with each other wherein said coupling of the two connecting elements is only maintained until a predetermined pulling force is reached and hereafter the two connecting elements are released from each other. The coupling element may be a weakened section of the connecting line which breaks at a predetermined pulling force, a spring-biased coupling wherein the spring force determines the pulling force required to release the coupling or the like.

According to a further preferred embodiment wherein a source of oxygen is provided in the passenger service unit and oxygen is supplied via a flow connecting line out of the passenger service unit to the oxygen mask it is preferred that said coupling element is connected to a starter unit integrated in said passenger service unit and adapted to start oxygen supply out of said source of oxygen source, wherein said starter unit is adapted to start oxygen supply out of said oxygen source if a pulling force along the connecting line exceeds a lower pulling force start level, said lower pulling force start level being below the predetermined lower pulling force. According to this embodiment a starter unit is integrated into the passenger service unit and is activated by a pulling force along the connecting line. This pulling force shall be stronger than a predetermined lower pulling force start level to avoid accidental start up of the oxygen supply. However, the lower pulling force start level shall be below the predetermined lower pulling force required to separate the oxygen mask from the passenger service unit. By this, it is possible that the passenger first initiates the oxygen supply by applying a pulling force exceeding a certain lower limit but not exceeding a predetermined second limit and to receive immediate oxygen supply via the connecting line. Hereafter, the passenger may apply a stronger pulling force to release the oxygen mask from the passenger service unit if this required, e.g. for an emergency quick exit procedure. It is to be understood that this embodiment may have a lower pulling force start level and a lower pulling force which are different from each other such that the passenger may not accidentally release the oxygen mask from the passenger service unit to early. Further, it is to be understood that the coupling element may be adapted to separate only after two pulling forces have been applied one after the other, i.e. the coupling element does not separate upon a first pulling force independent from the magnitude of said pulling force. In this preferred design option a first pulling force will in any case initiate the oxygen supply by activating the starter unit but will in no case separate the oxygen mask from the passenger service unit and a subsequent second pulling action may release the oxygen mask from the passenger service unit.

According to a further preferred embodiment wherein the source of oxygen is arranged at the oxygen mask and the connecting line is a wire, rope or the like, it is preferred that said coupling element is connected to a starter unit integrated in said oxygen mask and adapted to start oxygen supply out of said source of oxygen source, wherein said starter unit is adapted to start oxygen supply out of said oxygen source if a pulling force along the connecting line exceeds a lower pulling force start level, said lower pulling force start level being below the predetermined lower pulling force. According to this embodiment, the starter unit is positioned at the oxygen mask and is activated by a pulling force which is greater than a lower pulling force start level. Again, the oxygen mask may be released from the passenger service unit by applying a pulling force which is above the lower pulling force wherein said lower pulling force is greater than said lower pulling start level. It is to be understood that this embodiment may be designed in a similar way like the embodiment described beforehand, in particular the separation of the oxygen mask from the passenger service unit may require a second pulling force along said connecting line independent from the magnitude of said pulling force as explained beforehand.

According to a further preferred embodiment said chemical reaction component is an integral part of said oxygen mask, in particular is integral with said oxygen mask. It is particularly preferred to provide the chemical reaction component as an integral part or make it integral with the oxygen mask to provide a compact design of the oxygen mask easy to handle according to the invention. Still further it is preferred that said oxygen mask further comprises a flexible buffer connected to said mask body, wherein said flexible buffer is connected to said mask body via said chemical reaction component. Such a flexible buffer may be bag or the like and serves to take up oxygen enriched air or exhaled oxygen depleted air of the passenger. It is to be understood that according to a first design option the exhaled air may be stored in the oxygen bag and is directed through the chemical reaction component if the passenger inhales again to be enriched with oxygen during this inhaling cycle. According to a second design option the exhaled air may be directed through the chemical reaction component and enriched during the exhaling cycle. In this case, the oxygen enriched air is stored in the flexible buffer and the passenger may inhale said oxygen enriched air during the inhaling cycle directly out of said flexible buffer. According to a third design option the exhaled air may be directed through the chemical reaction component during the exhaling cycle to be enriched with oxygen, then stored in the flexible buffer and being directed through the chemical reaction component again during the inhaling cycle and thereafter enter the mask body. In this design option the air passes twice through the chemical reaction component in one breathing cycle thus enforcing the chemical reaction therein.

According to a still further preferred embodiment the oxygen supply device may be further improved an exhaling valve interconnected between the chemical reaction component and the flexible buffer, an inhaling valve interconnected between the mask body and the flexible buffer, wherein said exhaling valve is adapted to open if a pressure in the chemical reaction component is higher than in the flexible buffer and to close if a pressure in the flexible buffer is higher than in the oxygen mask and wherein said inhaling valve is adapted to open if a pressure in the flexible buffer is higher than in the oxygen mask and to close if a pressure in the chemical reaction component is higher than in the flexible buffer.

This preferred embodiment serves to direct the exhaled air in a circuit wherein oxygen enriched air is provided to the mask body via an inhaling valve and oxygen depleted air is directed from the mask body via an exhaling valve. This embodiment allows to reduce the dead volume of possible oxygen-pure air in a supply line or any supply components directing oxygen enriched air to the mask body and allows to provide a high amount of oxygen to the passenger in particular in the first phase of the inhaling process. In particular, the exhaling valve and the inhaling valve may be positioned directly in the mask body or be integral with the mask body.

According to a further preferred embodiment the chemical reaction material is KO2. Potassium dioxide is a material which has shown to be able to enrich exhaled air with oxygen during a long time and thus qualifies for a small and compact chemical reaction component positioned at the oxygen mask of a passenger oxygen supply system.

According to a further preferred embodiment the oxygen supply device according to the invention may be further improved by a control unit comprising a starting switch wherein said starting switch is coupled to said connecting line and enabled by a pulling force along said connecting line, wherein said control unit is connected to a source of oxygen and adapted to initiate supply out of said source of oxygen if said starting switch is enabled. Such a control unit may be an electronic or a mechanical unit like e.g. a mechanical switch, mechanical securing element pulled out by a pulling force out of a spring-biased starter unit or the like. The control unit may initiate the supply of oxygen by opening a valve, a seal or by producing a spark, an electric voltage or current to activate oxygen supply out of a pressurized oxygen source or out of a chemical oxygen generator respectively.

It is further preferred to provide a seal around said chemical reaction material wherein said control unit is adapted to break said seal if said starting switch is enabled. Such seal may safely prevent the chemical reaction material to deteriorate or to lose its chemical properties over time and thus makes sure to provide oxygen to the passenger in an emergency situation and to provide long maintenance cycles at the same time.

A further aspect of the invention is A method for rescuing a passenger of an aircraft in an emergency situation, comprising the steps of presenting an oxygen mask having a mask body to the passenger wherein said oxygen mask drops out of a passenger service unit and is connected to said passenger service unit via a connecting line, providing oxygen out of a startup oxygen source, in particular a chemical oxygen generator or a pressurized oxygen source to the passenger via said oxygen mask in an initial start-up phase, directing exhaled air out of said mask body to a chemical reaction component, conducting a chemical reaction in said chemical reaction component, wherein said exhaled air reacts with a chemical reaction material to produce oxygen and/or to reduce carbon dioxide in said exhaled air, directing oxygen enriched or carbon dioxide-depleted air out of said chemical reaction component to the mask body, separating said oxygen mask from said passenger service unit by decoupling said connecting line.

The method may be improved in that said startup oxygen source is positioned in the passenger service unit and said connecting line is a flexible tube for directing initial startup oxygen from said passenger service unit to said oxygen mask.

Alternatively, said startup oxygen source is integral with the oxygen mask and said connecting line is a wire or rope.

BRIEF DESCRIPTION OF THE DRAWINGS

Preferred embodiments of the invention are shown in the figures.

DETAILED DESCRIPTION OF THE DRAWINGS

Figure 1:
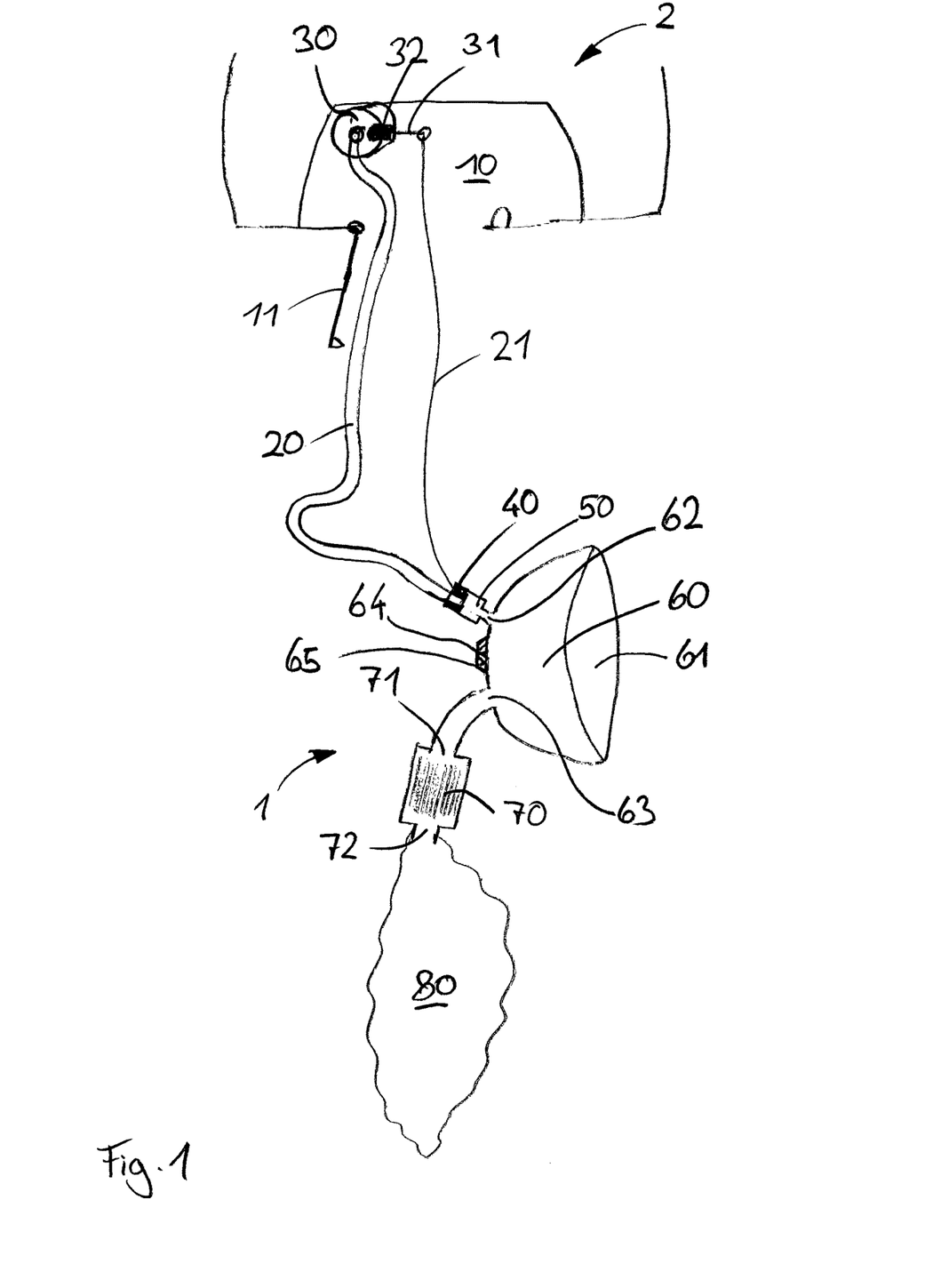
FIG. 1 shows a simplified schematical set up of a first embodiment of an oxygen device according to the invention, FIG. 1a the embodiment shown in FIG. 1 in a released condition.
Figure 1A:
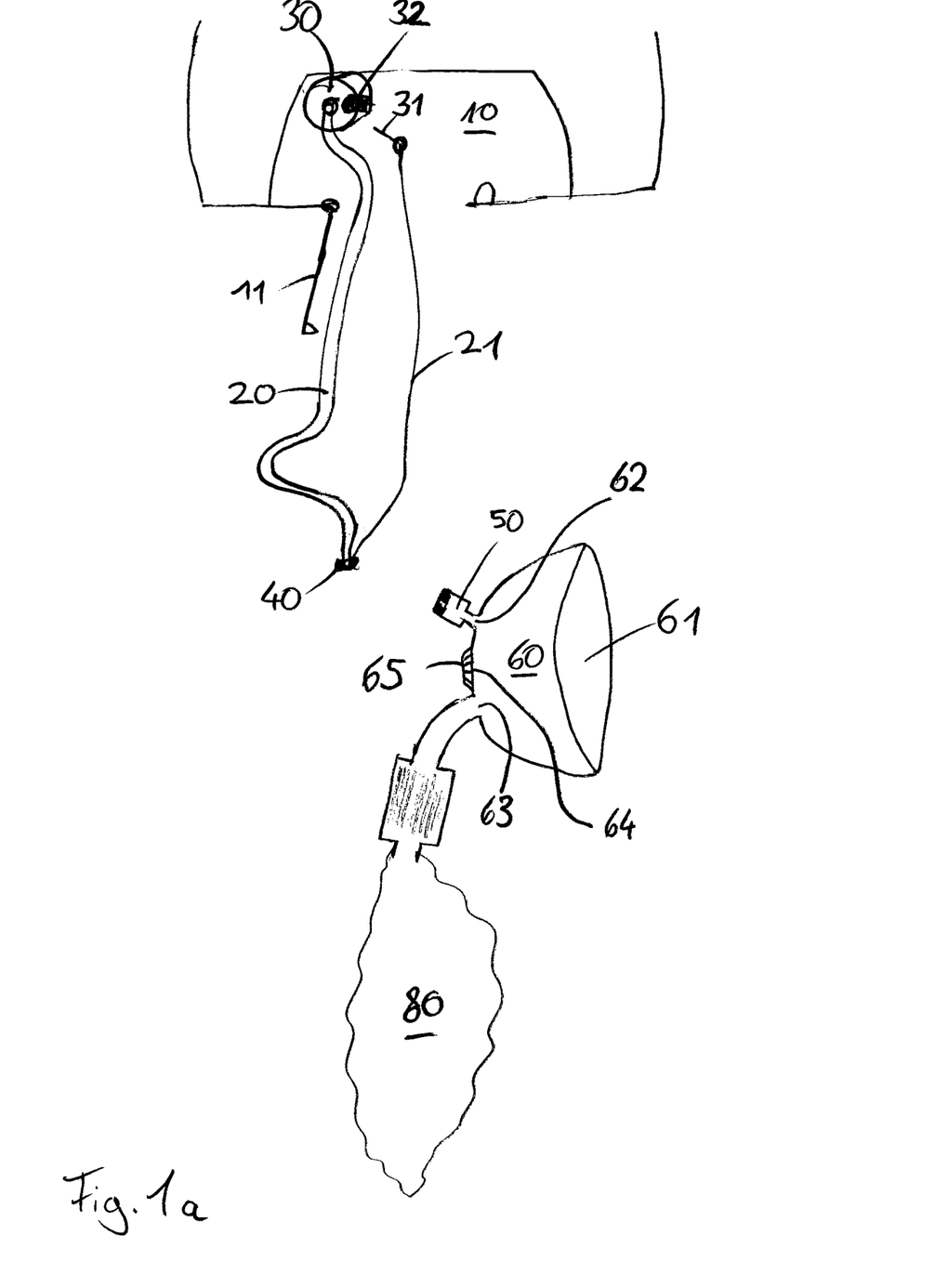

FIGS. 1 and 1a show a first embodiment of the invention in an emergency situation. An oxygen mask 1 has dropped out of a passenger service unit 2 which is arranged as a sealing compartment inside an aircraft cabin. The passenger service unit 2 comprises a storing space 20 wherein the oxygen mask 1 can be stored in regular flight condition. A cover lid 11 on the bottom side of said storing space can be released and opened to the outside of the storing space thus opening the storing space in the direction of gravity thus effecting a falling out of the oxygen mask 1.

The oxygen mask is connected to the passenger service unit 2 via a connecting line 20, 21. Said connecting line comprises a tether 21 and a flexible tube 20. The flexible tube is connected on the upper and to a chemical oxygen generator 30 and arranged in the passenger service unit. The downside end of the flexible tube is connected to a coupling element 40.

The downside end of the tether 21 is connected to the coupling element, too. The upside end of the tether 21 is connected to a releasable pin 31 which is part of a starter unit 32 attached to the chemical oxygen generator 30.

The coupling element 40 is integral with a control unit 50 which is attached to a mask body 60.

The mask body 60 comprises a large opening 61 for covering mouth and nose of a passenger. Further, a first small opening 62 is provided in said mask body 60, said first opening 62 being in fluid connection with the flexible hose 20 via said control unit 50 and said coupling element 40. Further, a second small opening 63 is present in the mask body 60. Said second opening 63 connects the interior of the mask body 60 with a chemical reaction component 70. Said chemical reaction component 70 comprises a first opening in fluid connection with the mask body 60 and a second opening 72 in fluid connection with a flexible bladder 80.

Finally, the mask body 60 comprises a third small opening 64 with integrated check valve 65.

The function of the emergency oxygen device according to the first embodiment is explained in detail with reference to FIGS. 1, 1a now. In regular flight condition the oxygen mask is completely stored in the storing space 10 of the passenger service unit. In case of an emergency situation requiring supply of oxygen to the passenger the cover lid is released and opened and the oxygen mask 1 falls out of the storing space to be presented to the passenger. The tether 21 holds the oxygen mask 1 in a predetermined position wherein it is easy for the passenger to grasp the oxygen mask.

The passenger will grasp the oxygen mask 1 and pull it downwards with a first pulling force. This first pulling force will affect release of the releasable pin 31 out of the starter unit 32. This pulling out of the pin 31 out of the starter unit 32 will effect a spark which activates the chemical oxygen generator to produce oxygen. The chemical oxygen generator 30 comprises oxygen in a chemically bound form selected from the groups of inorganic superoxides, chlorates, perchlorates and ozonides. Preferably, the chemical oxygen generator comprises sodium chlorate as a main ingredient. The oxygen produced in an exothermic reaction in the chemical oxygen generator is directed to the mask body via the flexible hose 20. The control unit 50 comprises an inhaling valve which opens if the passenger applies a low pressure to the inside of the mask body 60 and thus a partition of oxygen is provided to the mouth and nose of the passenger via the opening 61. This partition corresponds to an amount of oxygen produced by the chemical oxygen generator in the foregoing exhaling cycle. As soon as this amount of oxygen is exhausted the passenger may apply a larger vacuum to the inside of the mask body affecting an opening of the check valve 65. By this, ambient air is drawn into the mask body to allow the passenger to complete the inhaling cycle. This ambient air may have a low oxygen content but since the first partition of concentrated oxygen is delivered into the lung of the passenger this second partition of pure oxygen air only serves to fill the mouth and respiratory ducts of the passenger and does not require to be rich of oxygen herefor.

After having inhaled this first and second partition through said first opening 62 and said third opening 64 the passenger will exhale the air. If the passenger applies a positive pressure to the inside of the mask body in this exhaling cycle the valve unit comprised in the control unit 50 will close and the check valve 65 will close. The exhaling air will thus flow through the second opening 63 into the chemical reaction component 70. The chemical reaction component 70 comprises potassium dioxide. This potassium dioxide reacts with the carbon dioxide of the exhaled air in an exothermic reaction as follows:

$$4KO_2 + 2CO_2 = 2K_2CO_3 + 3O_2.$$

Thus, carbon dioxide contained in the exhaled air is chemically bound in the chemical reaction component and oxygen is produces therein. It is an important aspect of the chemical reaction material comprised in the chemical reaction component to have the ability to bind carbon dioxide out of the exhaled air and to produce oxygen out of the exhaled air at the same time.

It is to be understood that other materials might be used as a chemical reaction component as well. This may comprise lithiumhydroxide and/or breathing lime or calcium carbonate. In particular, the chemical reaction component may be adapted to extract carbondioxide out of the exhaled air only but to not produce additional oxygen. Such a chemical reaction component may be used in connection with a small oxygen source like e.g. a small oxygen pressure tank or a small chemical oxygen generator. Using such chemical reaction component will allow the passenger to participate in evacuation process of an aircraft without the risk of fainting due to carbon dioxide intoxication.

After having passed through the chemical reaction component 70 from the first opening 71 to the second opening 72 the oxygen enriched and carbon dioxide depleted exhaled air flows into the flexible bladder 80 and is temporarily stored therein. The flexible bladder may be dimensioned in such a way to take up the whole exhaled air out of one breathing cycle of the passenger. Alternatively, the flexible bladder may be dimensioned in such a way to take up only a part of said exhaled air whereas a remaining part is exhaled through an exhale valve (not shown) into the ambient air inside the cabin. The check valve 65 may be adapted to open upon a high pressure inside the oxygen mask and thus allow the remaining second part of the exhaling air volume to pass into the ambient air.

In the subsequent breathing cycle the passenger will take up first the oxygen produced by the chemical oxygen generator during the foregoing exhaling cycle. Hereafter the passenger will take up the exhaled air out of the flexible bladder 80. During this taking up of the exhaled air the exhaled air passes again through the chemical reaction component 70 thus being further enriched with oxygen and depleted from carbon dioxide.

The chemical oxygen generator 30 is dimensioned to provide oxygen for less than one minute. It is to be understood, that the chemical oxygen generator may be adapted to supply oxygen for a shorter period of time like e.g. only 30 or 45 seconds and for a longer period of time like e.g. 1.5 minutes, 2 minutes or 5 minutes depending on the configuration of the system components. It is usually desired that after such time period the chemical reaction in the chemical reaction component 70 has fully started and the passenger will receive sufficient oxygen out of the chemical reaction in the chemical reaction component 70 to maintain his vital functions.

Hereafter, the passenger may pull again the oxygen mask 1 to himself thus affecting a second pulling force on the coupling element 40. This second pulling force will affect a release of the coupling element and thus cut the last connection of the oxygen mask 1 to the passenger service unit 2 which was present by the flexible hose. The passenger may then move inside the cabin with the oxygen mask 1 being permanently supplied with oxygen enriched and carbon dioxide depleted air. In particular, the passenger may use his mask during evacuation of the passengers to the outside of the aircraft cabin after landing of the aircraft.

Figure 2:
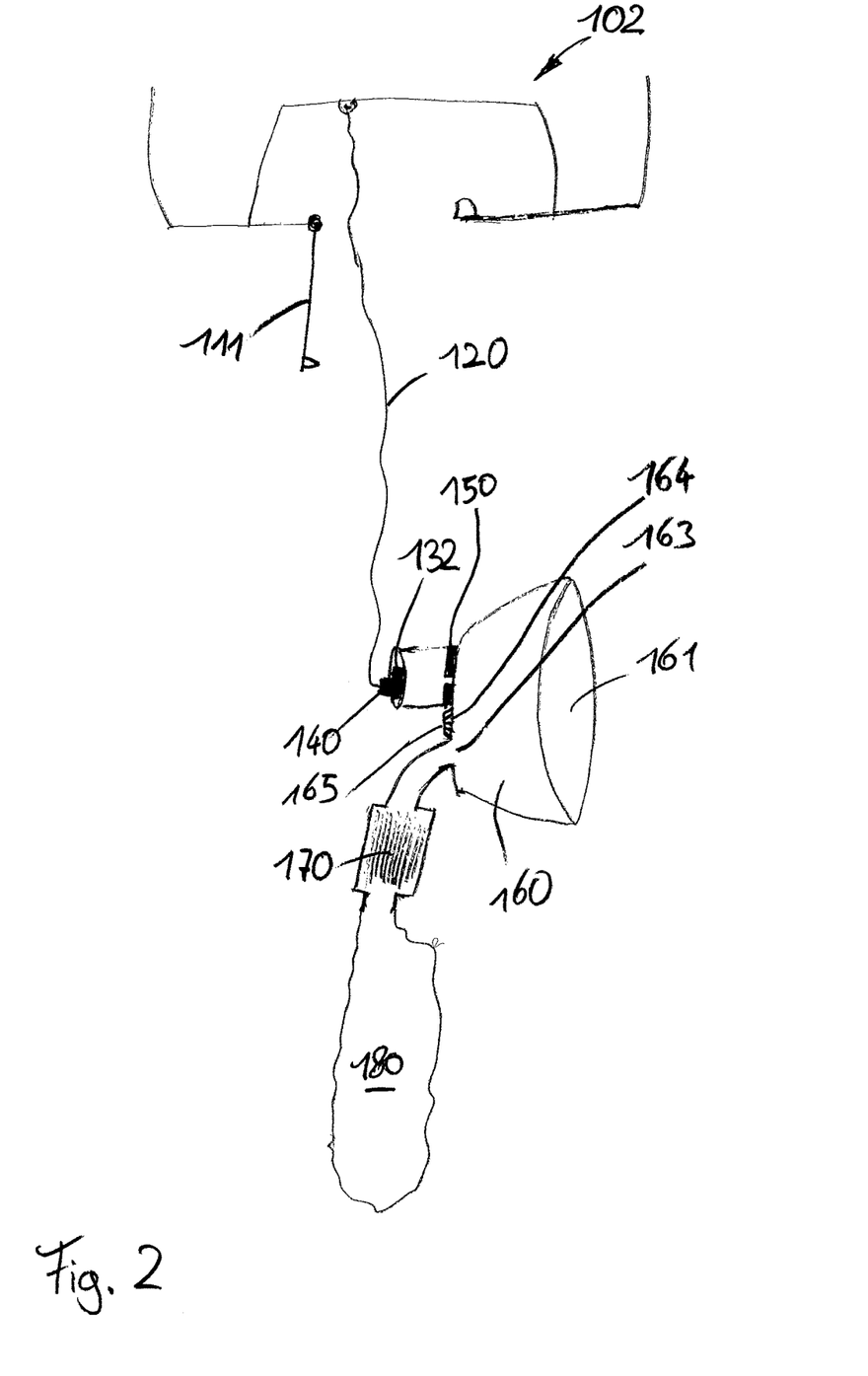
FIG. 2 shows a simplified schematical set up of a second embodiment of an oxygen device according to the invention, FIG. 2a the embodiment shown in FIG. 2 in a released condition.
Figure 2A:
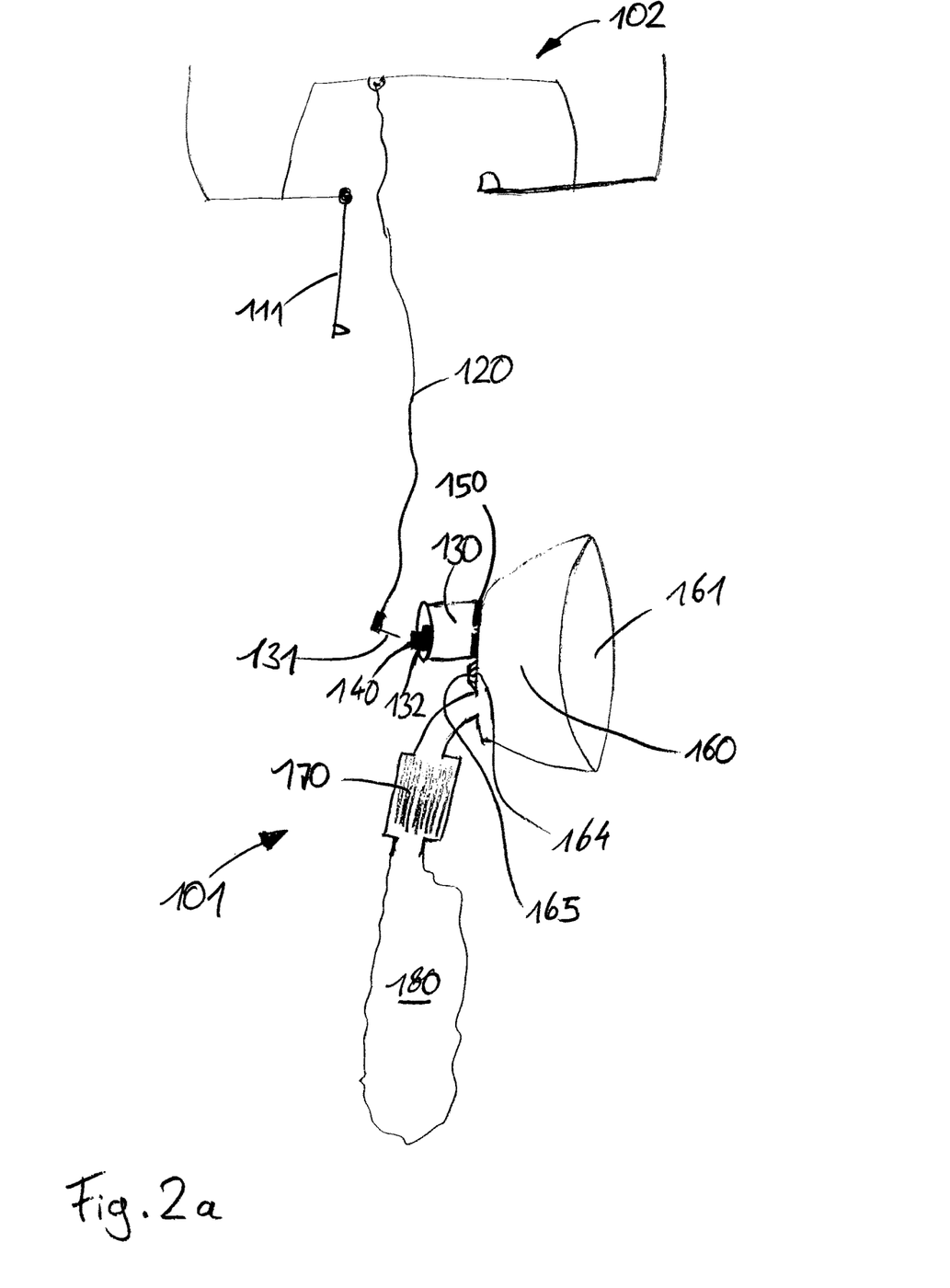

FIGS. 2 and 2a show a second embodiment of the emergency oxygen device according to the invention. This second embodiment comprises an oxygen mask 101 having a mask body 160 with a large first opening 161 and small third opening 163 connecting the interior of said mask body 160 to a chemical reaction component 170 which is connected to a flexible bladder 180. These components correspond to the mask body 60 with the first opening 61, the third opening 63, the chemical reaction component 70 and the flexible bladder 80 of the first embodiment in design and function.

Further, a force opening 164 with a check valve 165 is provided at the mask body 160 corresponding to the force opening 64 with check valve 65 of the first embodiment in design and function.

As an important difference to the first embodiment the emergency oxygen device according to the second embodiment comprises a source of oxygen which is part of the oxygen mask 101. Said source of oxygen is a chemical oxygen generator 130 with integrated control unit 150 and a starter unit 132 attached thereto. The chemical oxygen generator 130 is directly attached to the mask body 160. The starter unit 132 is connected via releasable pin 131 to a tether 120 at one end of said tether. The other end of said tether 120 is connected to a fixing point inside the passenger service unit 102.

The function of the second embodiment is explained with reference to FIGS. 2, 2a in detail now:

In regular flight condition the oxygen mask 101 is completely stored in the passenger service unit 102. IN an emergency situation a cover lid 111 is opened and the oxygen mask falls out of the passenger service unit 102. The oxygen mask 101 is hold by the tether 120 and presented to the passenger to allow easy grasping of the oxygen mask. In this situation the passenger may decide or be instructed to start the oxygen flow at a certain time.

If the passenger wishes to receive oxygen out of the oxygen mask 101 he will grasp the oxygen mask and pull it towards himself. In this case a pulling force is applied to the tether 120 affecting the releasable pin 131 to be pulled out of the coupling element 140 which is part of the starter unit 132. This pulling out action will ignite the chemical oxygen generator 130 and initiate a chemical reaction inside said chemical oxygen generator wherein oxygen is produced out of sodium chlorate.

The passenger will inhale the so produces oxygen out of the chemical oxygen generator 130 through the control unit 150 as a first partition of the inhaled air volume. This first partition of oxygen is produced during the foregoing exhaling cycle.

If no more generated gaseous oxygen is present in the chemical oxygen generator 130 the check valve 165 will open and allow the passenger to draw a second partition of the inhaling air volume into the mask body and to fill the respiratory ducts, the mouth and the nose with said second partition. This second partition may have a pure oxygen content which does not affect the supply of oxygen for vital functions to the passenger.

The chemical oxygen generator 130 is dimensioned to provide oxygen to the passenger for approximately 10-30 breathing cycles i.e. approximately one minute. Hereafter, the chemical reaction in the chemical reaction component 170 comprising potassium dioxide as described beforehand will have started completely and the passenger is supplied with oxygen enriched and carbon dioxide depleted air in a closed circuit.

In the second embodiment a singular pulling force is required to initiate the supply of oxygen to the passenger out of the chemical oxygen generator 130 and to release the oxygen mask 101 from the tether 120 and thus from the passenger service unit 102 at the same time. Thus, the passenger may immediately leave his seat after he applied said pulling force and started the oxygen supply when using the second embodiment of the invention.

The invention claimed is:

1. Aircraft passenger emergency oxygen supply device, comprising:
   an oxygen mask having a mask body with an oxygen-delivery opening for covering a mouth and/or a nose of a passenger, a first opening connecting said oxygen-delivery opening with a source of oxygen, the first opening comprising a control unit with an inhaling valve,
   a passenger service unit,
   a connecting line fixed to the mask body at a first end of the connecting line and having a coupling at a second end for coupling said connecting line to the passenger service unit, the connecting line comprising a coupling element,
   a chemical reaction component connected to the mask body for receiving exhaled air out of said mask body via a second opening, converting said exhaled air into supply air by a chemical reaction between said exhaled air and a chemical reaction material comprised in said chemical reaction component to produce oxygen-enriched air and for supplying said oxygen-enriched air as the supply air to the mask body,
   a flexible buffer connected to the mask body via the chemical reaction component,
   an exhaling valve interconnected between the chemical reaction component and the flexible buffer
   a second inhaling valve interconnected between the mask body and the flexible buffer, and
   a third opening with an integrated check valve,
   wherein:
   the inhaling valve opens when pressure from a first exhaling cycle is applied to an inside of the mask body and is below a predetermined threshold, wherein opening of the inhaling valve provides oxygen from the source of oxygen through the oxygen delivery opening,
   the integrated check valve opens when a vacuum from a first inhaling cycle is applied to the inside of the mask body, wherein opening of the integrated check valve draws ambient air through the check valve into the inside of the mask body,
   the integrated check valve closes when pressure from a second exhaling cycle is applied to the inside of the mask body that is above the predetermined threshold, and wherein closing of the integrated check valve draws the exhaled air through the second opening into the chemical reaction component,
   the exhaling valve opens if a pressure in the chemical reaction component is higher than in the flexible buffer and closes if a pressure in the flexible buffer is higher than in the oxygen mask,
   the second inhaling valve opens if a pressure in the flexible buffer is higher than in the oxygen mask and closes if a pressure in the chemical reaction component is higher than in the flexible buffer, and
   the coupling element is adapted to maintain the connection provided by the connecting line and the coupling element between the oxygen mask and the passenger service unit if a predetermined pulling force along the connecting line is not exceeded, and to release the connection provided by the connecting line and the coupling element between the oxygen mask and the passenger service unit if the predetermined pulling force along the connecting line is exceeded.

2. Oxygen supply device according to claim 1, wherein said connecting line is an oxygen supply line for connecting said mask body with the source of oxygen in said passenger service unit, wherein said source of oxygen is a chemical oxygen generator or a pressurized oxygen tank.

3. Oxygen supply device according to claim 1, wherein said connecting line is a wire or rope for connecting said mask body with a fixing point in said passenger service unit, wherein said oxygen mask further comprises a source of oxygen, wherein said source of oxygen is a chemical oxygen generator or a pressurized oxygen tank.

4. Oxygen supply device according to claim 1, wherein said coupling element is connected to a starter unit integrated in said passenger service unit and adapted to start oxygen supply out of said source of oxygen, wherein said starter unit is adapted to start an oxygen supply out of said source of oxygen if a pulling force along the connecting line exceeds a lower pulling force start level, said lower pulling force start level being below the predetermined pulling force.

5. Oxygen supply device according to claim 1, wherein said coupling element is connected to a starter unit integrated in said oxygen mask and adapted to start oxygen supply out of said source of oxygen, wherein said starter unit is adapted to start oxygen supply out of said source of oxygen if a pulling force along the connecting line exceeds a lower pulling force start level, said lower pulling force start level being below the predetermined lower pulling force.

6. Oxygen supply device according to claim 1, wherein said chemical reaction component is integral with said oxygen mask.

7. Oxygen supply device according to claim 1, wherein the chemical reaction material is $KO_2$.

8. Oxygen supply device according to claim 1, wherein the control unit further comprises a starting switch coupled to said connecting line and enabled by a pulling force along said connecting line, wherein said control unit is connected to the source of oxygen and adapted to initiate supply out of said source of oxygen if said starting switch is enabled.

\* \* \* \* \*